United States Patent [19]
White

[11] Patent Number: 5,539,485
[45] Date of Patent: Jul. 23, 1996

[54] ILLUMINATION DEVICE FOR PROVIDING CONTINUOUS DIFFUSE LIGHT ON AND OFF AN OBSERVING AXIS

[76] Inventor: Timothy P. White, 146 Lull Rd., New Boston, N.H. 03070

[21] Appl. No.: 331,882

[22] Filed: Oct. 31, 1994

[51] Int. Cl.[6] ................................................ G03B 29/00
[52] U.S. Cl. .............................. 354/76; 355/67; 355/70; 355/71
[58] Field of Search .................................. 354/76; 352/4, 352/89; 355/67, 70, 71

[56] References Cited

U.S. PATENT DOCUMENTS

| | | |
|---|---|---|
| 2,792,740 | 5/1957 | Haynes . |
| 2,926,559 | 3/1960 | Oppenheimer . |
| 2,934,601 | 4/1960 | Oppenheimer . |
| 3,322,487 | 9/1966 | Renner . |
| 3,558,894 | 1/1971 | Odone et al. . |
| 3,596,083 | 7/1971 | Lovering . |
| 3,944,336 | 3/1976 | Carr . |
| 3,984,157 | 10/1976 | Le Vantine . |
| 3,985,425 | 10/1976 | Clapp . |
| 4,067,026 | 1/1978 | Pappanikolaou . |
| 4,185,902 | 1/1980 | Plaot . |
| 4,341,449 | 7/1982 | Iwata et al. . |
| 4,555,635 | 11/1985 | Yoshida . |
| 4,561,722 | 12/1985 | Smetana . |
| 4,601,576 | 7/1986 | Galbraith . |
| 4,677,473 | 6/1987 | Okamoto et al. . |
| 4,691,231 | 9/1987 | Fitzmorris et al. . |
| 4,712,889 | 12/1987 | Schindl . |
| 4,791,534 | 12/1988 | Lindberg . |
| 4,816,686 | 3/1989 | Hara et al. . |
| 4,854,688 | 8/1989 | Hayford et al. . |
| 4,877,326 | 10/1989 | Chadwick et al. . |
| 4,882,498 | 11/1989 | Cochran et al. . |
| 4,972,093 | 11/1990 | Cochran et al. . |
| 4,991,947 | 2/1991 | Sander et al. . |
| 5,011,265 | 4/1991 | Tamamura et al. . |
| 5,039,868 | 8/1991 | Kobayashi et al. . |
| 5,051,825 | 9/1991 | Cochran et al. . |
| 5,060,065 | 10/1991 | Wasserman . |
| 5,072,127 | 12/1991 | Cochran et al. . |
| 5,155,558 | 10/1992 | Tannenbaum et al. . |
| 5,187,611 | 2/1993 | White et al. . |

*Primary Examiner*—Monroe H. Hayes
*Attorney, Agent, or Firm*—Davis, Bujold & Streck

[57] ABSTRACT

An illumination device for illuminating an object to be observed, by a machine vision camera of the like for example, with a continuous diffuse wide angle light which is supplied both along the viewing axis of the machine vision camera and off axis. The diffuser of the present invention is tilted with respect to the observation axis so that the diffuser is not viewable by the object to be observed. This provides better uniformity of the light which illuminates the object. A second diffuser may be utilized to provide illumination of the object with light of reduced intensity.

20 Claims, 6 Drawing Sheets

ILLUMINATION DEVICE FOR PROVIDING CONTINUOUS DIFFUSE LIGHT ON AND OFF AN OBSERVING AXIS

FIELD OF THE INVENTION

This invention pertains to an illumination device for illuminating an object to be observed, by a machine vision camera or the like for example, with a continuous diffuse wide angle light whose illumination is supplied both along the viewing axis of the machine vision camera and off axis.

BACKGROUND OF THE INVENTION

Robotic assembly machines often utilize video cameras to observe the component, part or work piece being handled, machined or assembled. For instance, in the assembly of electronic components, the chips or wafers are often assembled into printed circuit boards by robots utilizing video cameras to position the components and/or to inspect the assembled device for defects throughout the process.

In the microelectronics industry, solder pads on surface-mount devices are often observed by machine vision systems for assembly and manufacturing purposes. The accuracy and reliability of a machine vision system is critical for proper alignment of the numerous components which are to be mounted on a printed circuit board. For optimum alignment, solder pads must be clearly observed in high contrast with their background.

Components in many industries often utilize etched characters appearing on mirror like surfaces that serve to identify the components and to accurately position them during assembly. In order to permit a clear image of the characters to be produced in the camera for accurate manipulation of the parts by the robotic handling equipment, it is important that the observed object be properly illuminated.

Proper illumination of many different shiny and uneven surfaces, e.g. solder connections, foil packaging, ball bearings, etc., is critical if high quality robotic assembly is to be achieved. However, such shiny and uneven surfaces are difficult to illuminate for accurate video imaging, and this creates a need for improved illumination of such objects being observed by machine vision cameras.

When using previously available illumination systems to illuminate work pieces having uneven, highly reflective surfaces, the uneven reflection of light from these surfaces frequently produces erroneous images and signals within the camera thereby possibly resulting in an erroneous signal or incorrect/inaccurate measurement. Errors of one or two thousands of an inch in a fiducial location measurement for a single component are sufficient to ruin a large and expensive circuit board. Furthermore, previously available illumination systems for robotic handling of items have not produced a light which is uniform over the entire object being observed. As a result, the reflected image suffers from erroneous shadows, glints and glare thereby rendering it difficult to determine the precise location or quality of the object.

To date, many illumination devices have been developed to provide substantially uniform illumination of an object to be viewed, but such known illumination devices are fairly large and cumbersome and are thus difficult to integrate into an electronic manufacturing process. For example, one of the Inventor's known light system might occupy a volume of 300 cubic inches and weigh several pounds, thereby adding to the costs and expense in constructing machine vision equipment in a very competitive industry. It is desirable to manufacture a miniature illumination device which may occupy 8 cubic inches or less and only weigh a few ounces. Such miniaturization allows significant cost savings and lessens the expense of the machinery for inspecting manufactured products.

Figure 12:
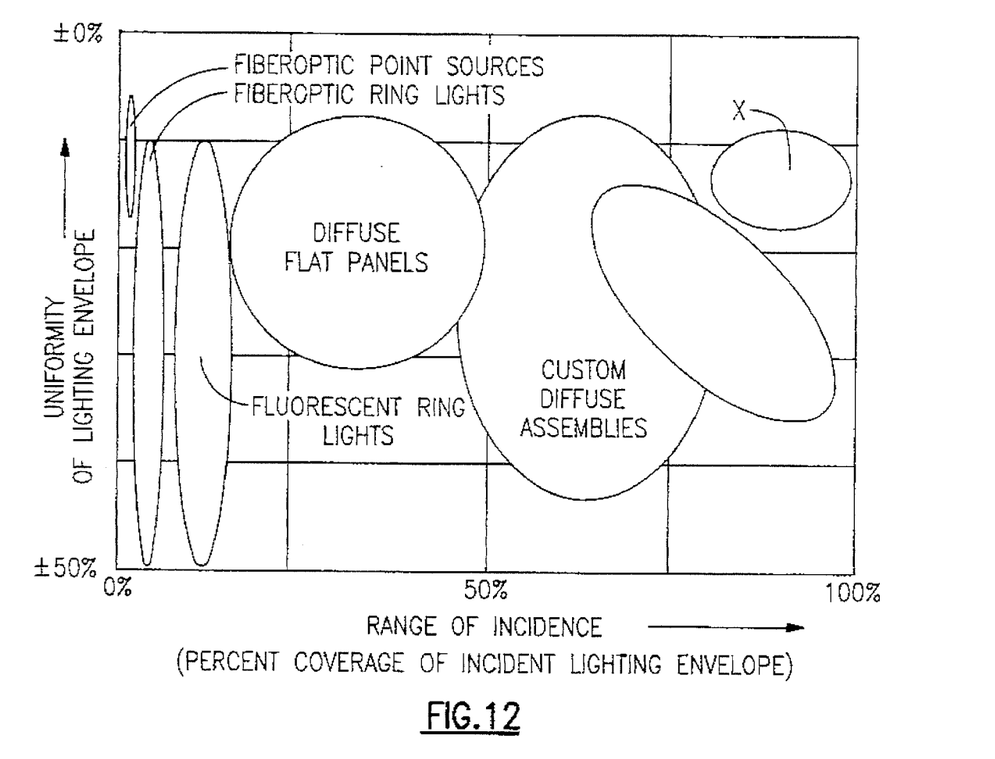
FIG. 12 is a graph depicting the characteristics of a "diffuse" light.

The term "diffuse", as used in this patent application, means a light source which is uniformly dispersed over a broad range of incident angle of azimuth and elevation with respect to the object being observed, and the light source approaches complete coverage over the area where the light is directed, i.e. greater than 80% of the possible angular range of incident light—approaching area X in FIG. 12. The term "invisible", as used in this patent application when referring to the diffuser and the object to be observed, means that the surface emitting the diffused light from the diffuser is at an angle greater than a critical value with respect to the object such that that emitting surface can not directly illuminate the object, i.e. only indirect illumination of the object by reflection of light of the side wall(s) of the housing can occur.

Wherefore it is an object of the invention to overcome the above noted drawbacks of the prior art illumination devices.

It is another object of the present invention to develop an improved continuous diffuse illumination device for machine vision systems to precisely determine the location of the object being observed.

It is a further object of the invention to develop an improved diffuse wide angle illumination field to improve image quality and uniformity of appearance of uneven specular surfaces, such as those found in the electronic and pharmaceutical manufacturing processes, e.g. pills, capsules, and their packaging.

A still further object of the invention is to provide an adaptor for an existing diffuse illumination device that increases the uniformity of the illumination provided thereby.

Yet another object of the invention is to increase (e.g. double) the brightness of the light reflected by the beam splitter to make such reflected light appear more equal in brightness to the light reflected by the diffusely reflecting inner surfaces of the surrounding housing structure.

Yet another object of the invention is to reduce the brightness of the direct off-access light from the diffuser to the object to the same range of brightness as the light reflected by the beam splitter and the surrounding housing structure.

Still another object of the invention is to minimize uneven illumination of the object to be observed and the area adjacent the object, e.g. maximize the range of elevational angles of incident which commonly occur with simple beam-splitter illumination devices (Carr et al. for example) where the beam splitter is planar and its bottom edge is substantially flush with the bottom aperture of the housing.

SUMMARY OF THE INVENTION

These and other objects of the invention are realized by an illumination device for illuminating an object to be observed by a camera along an observation axis extending from the camera to the object, said illumination device comprising a housing having at least one aperture therein aligned with an observation axis; a partially reflective beam splitter being supported by said housing and being positioned obliquely relative to the observation axis adjacent said at least one aperture; a light source being arranged to cast light on a first surface of said beam splitter; and a diffuser being positioned between said first surface of said beam splitter and said light source for diffusing light from said light source as the light passes through said diffuser to said beam splitter; wherein at least a first portion of said diffuser, facing said beam splitter, is inclined a sufficient distance relative to the observation axis so that at least the first portion of the surface of said diffuser facing said beam splitter is invisible by any portion of an object to be observed when the object is positioned along the observation axis.

The invention also relates to an illumination device, for illuminating an object to be observed by a camera along an observation axis extending from the camera to the object, comprising a housing having at least one aperture therein aligned with an observation axis; a partially reflective beam splitter being supported by said housing and being positioned obliquely relative to the observation axis adjacent said at least one aperture; a light source being arranged to cast light on a first surface of said beam splitter; and a diffuser being positioned between said first surface of said beam splitter and said light source for diffusing light from said light source as the light passes through said diffuser to said beam splitter; wherein at least a first portion of said diffuser facing said beam splitter is inclined a sufficient distance relative to the observation axis such that an emitting surface of said diffuser is completely hidden from direct viewing by the object to be observed, when the object is positioned on the observation axis and during use of said illumination device, whereby at least the first portion of said diffuser only indirectly illuminates the object to be observed by reflection.

The invention finally relates to a method of illuminating an object to be observed by a camera along an observation axis extending from the camera to the object, said method comprising the steps of utilizing a housing having at least one aperture therein aligned with an observation axis; supporting a partially reflective beam splitter within said housing, and positioning said partially reflective beam splitter obliquely relative to the observation axis adjacent said at least one aperture; arranging a light source to cast light on a first surface of said beam splitter; and positioning a diffuser between said first surface of said beam splitter and said light source for diffusing light from said light source as the light passes through said diffuser to said beam splitter; and inclining at least a first portion of said diffuser facing said beam splitter a sufficient distance relative to the observation axis so that at least the first portion of the surface of said diffuser facing said beam splitter is not directly visible by any portion of an object to be observed when the object is positioned along the observation axis.

BRIEF DESCRIPTION OF THE DRAWINGS

The invention will now be described, by way of example, with reference to the attached drawings, in which.

DESCRIPTION OF THE PREFERRED EMBODIMENTS

Turning now to FIGS. 1–4, the first embodiment of the invention will now be described in detail. The on-axis continuous diffuse illumination device 2 of the invention is particularly suitable for use with a computer controlled robotic assembly or other manufacturing apparatus 6 that utilizes a video camera 10 to image an object 12 on a support table 14 by viewing the object along an observation axis 16 as shown in the FIG. 1. With such a robotic apparatus, electronic signals from the camera 10, resulting from the imaging of the object 12, are used to control the computer 4 which in turn controls the operation of the robotic assembly or other manufacturing apparatus 6. The object 12 may be supported on a movable table, conveyor or moveable jig constituting a part of the robotic apparatus permitting the object to be very accurately located with respect to the observation axis 16, the apparatus, or other component(s) with which the object is to be associated.

As shown in FIGS. 1–4, a housing 18 encases the various components of the continuous diffuse illumination device 2. The housing 18 comprises a first pair of spaced apart parallel side walls 19, a second pair of spaced apart parallel side walls 20 and a roof wall 21 and a base wall 21'. An aperture 22 is formed in both the roof wall 21 and the base wall 21' and the apertures 22 are concentric with one another and located along the observation axis 16. The housing accommodates therein at least one light source 28 adjacent one of the side walls 19, a beam splitter 23 located remote from the light source 28 and positioned along the observation axis, a light diffuser shown generally as 24 located between the light source 28 and the beam splitter 23, and a light trap 26 supported by the side wall 19 opposite the side wall 19 adjacent the light source 28. The arrangement of these components is such that the light source 28 casts light upon the diffuser 24 which, in turn, diffuses the light from the light source 28 and casts the diffused light upon the beam splitter 23 which reflects a desired portion of the diffused light toward the object 12. Any nonreflected light which passes through the beam splitter 23 is absorbed by the light trap 26 located adjacent the beam splitter 23.

Figure 1:
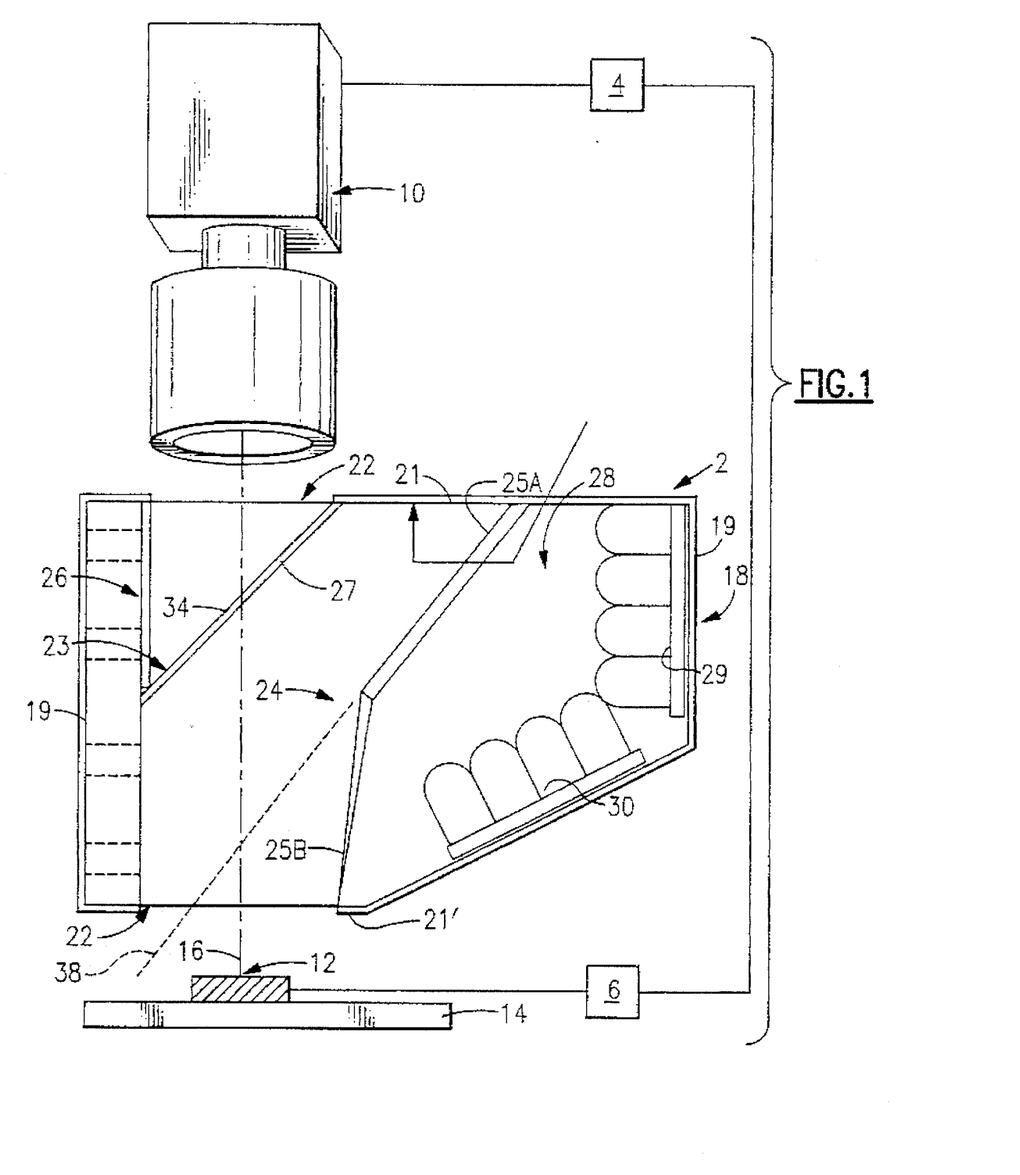
FIG. 1 is a diagrammatic illustration of an improved continuous diffuse illumination device, equipped with an inspection camera and other associated assembly equipment, providing light both along the observation axis and off-axis according to the present invention.
Figure 2:
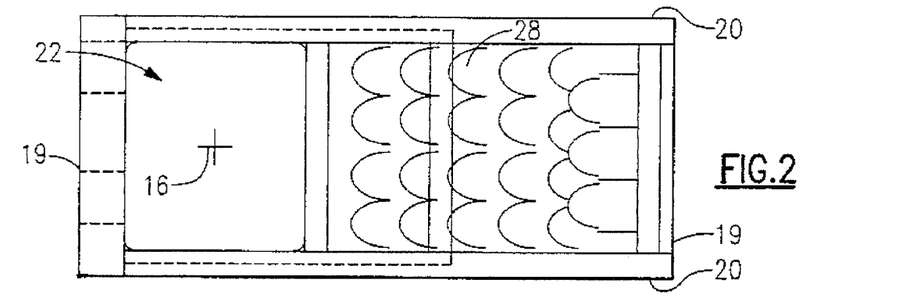
FIG. 2 is a diagrammatic top plan illustration of the continuous diffuse illumination device of FIG. 1 prior to installation of the inspection camera and other associated assembly equipment.
Figure 3:
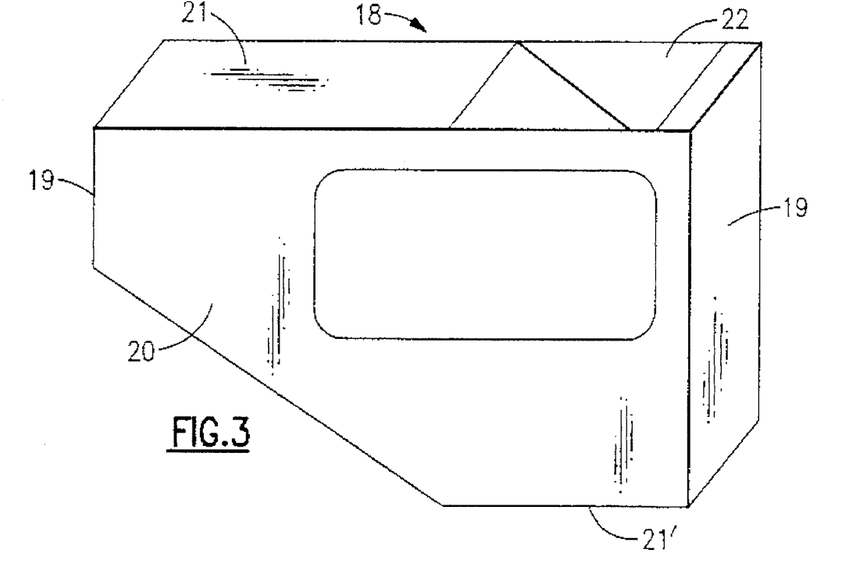
FIG. 3 is a diagrammatic perspective illustration of FIG. 1 prior to installation of the inspection camera and other associated assembly equipment.

The beam splitter 23 has a partially reflective first surface 27. A desired portion of the light e.g. approximately half of the light, from the diffuser 24 impacting upon the reflective first surface 27 of the beam splitter 23 is reflected toward the object 12, while the remainder of the light passes through the beam splitter 23 and is absorbed by the light trap 26. Likewise, a portion of the light reflected back by the object 12 is transmitted toward and through the beam splitter 23 along the observation axis 16 for viewing by the camera 10. The light returned to the camera 10 is used to determine the precise shape, orientation, and/or other characteristics of the object 12. It is well known in this art how to use of the light returned to the camera 10 to determine the shape and orientation of the object 12, and thus a detail description concerning the same is not provided herein.

An important aspect of the present invention is that at least a first diffuser portion 25A is inclined with respect to the observation axis 16. In all prior art known devices of which the inventor is aware, the diffuser 24 is aligned substantially parallel to the observation axis and thus provides direct lighting of the object 12 to be observed. The first diffuser portion 25A, according to the present invention, is inclined relative to the observation axis, e.g. between an angle of about 5° and 45° and preferably approximately 25° to 40° with respect to the observation axis, so that light diffused by the first diffuser portion 25A cannot directly illuminate the object. Accordingly, light from the first diffuser portion 25A is reflected off either the inner roof wall 21 of the housing 18 or the beam splitter 23 and thus indirectly illuminates the object 12 to be observed. The inner surface of the roof wall 21 as well as the inner surface of the side walls 20 of the housing 18 can be painted with a white, gray, or another desired color or shade of paint or some other diffusely reflective substance so as to provide desired efficiency of reflection of the light diffused by the diffuser 24 onto the object to be observed.

Accordingly, the first diffuser portion 25A is not directly visible by the object 12 to be observed, i.e. the first diffuser portion 25A is inclined such that it lies along a plane indicated by dashed line 38 which is to the left of the object 12 to observed and thus can not directly illuminate the object. The second diffuser portion 25B extends vertically down from a second edge of the first diffuser portion such that a portion of the light passing through by that portion directly illuminates the object 12 and a remaining portion of the diffused light is reflected by the inner surface of the side walls 19, 20 toward the object 12.

In this manner, a portion of the light diffused by the diffuser 24 directly illuminates the object 12 over a first range of incidence angles and another portion of the light from the diffuser is reflected by the reflective second surface 27 of the beam splitter illuminating the object 12 over a second range of incidence angles.

Figures 9, 10, 11:
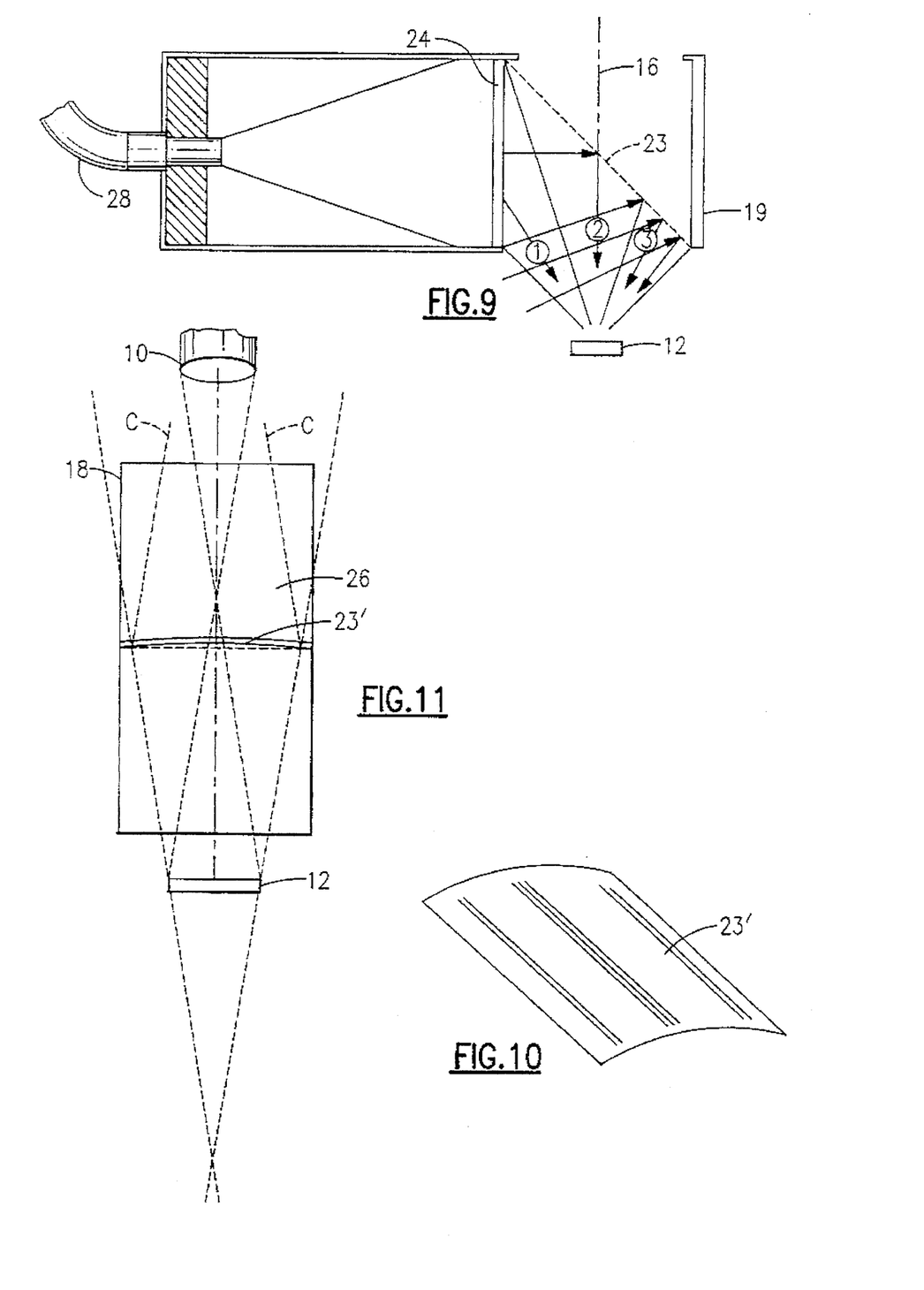
FIG. 9 is a diagrammatic plan view of a prior art illumination device showing the area which is poorly and/or non-uniformly illuminated.
FIG. 10 is a perspective illustration of a curved beam splitter according to the present invention.
FIG. 11 is a diagrammatic end-view cross-sectional illustration of the object and camera using the curved beam splitter of FIG. 10 and showing its optical effect.

In order to cause light to be reflected to the object 12 from the entire surface of the beam splitter 23, rather than being limited to an area of the beam splitter surface bounded on its lower side by a point reflecting a ray of light from the bottom edge of the diffuser 24 to the object 12, as generally occurs with known illumination devices, making use of beam splitters reflecting diffuse light sources adjacent to the observation axis, the present invention increases the length of the side walls 19, 20 so that the spacing of the roof wall 21 from the base wall 21' is increased, e.g. substantially doubled, over the proportional spacing of the roof and base walls of the known illumination devices. The extended side walls, according to the present invention, provide greater surface area for reflecting the light passing through the diffuser 24 and results in a substantially greater range of angle of incident uniform lighting of the object 12 to be observed (FIG. 9).

Figure 4:
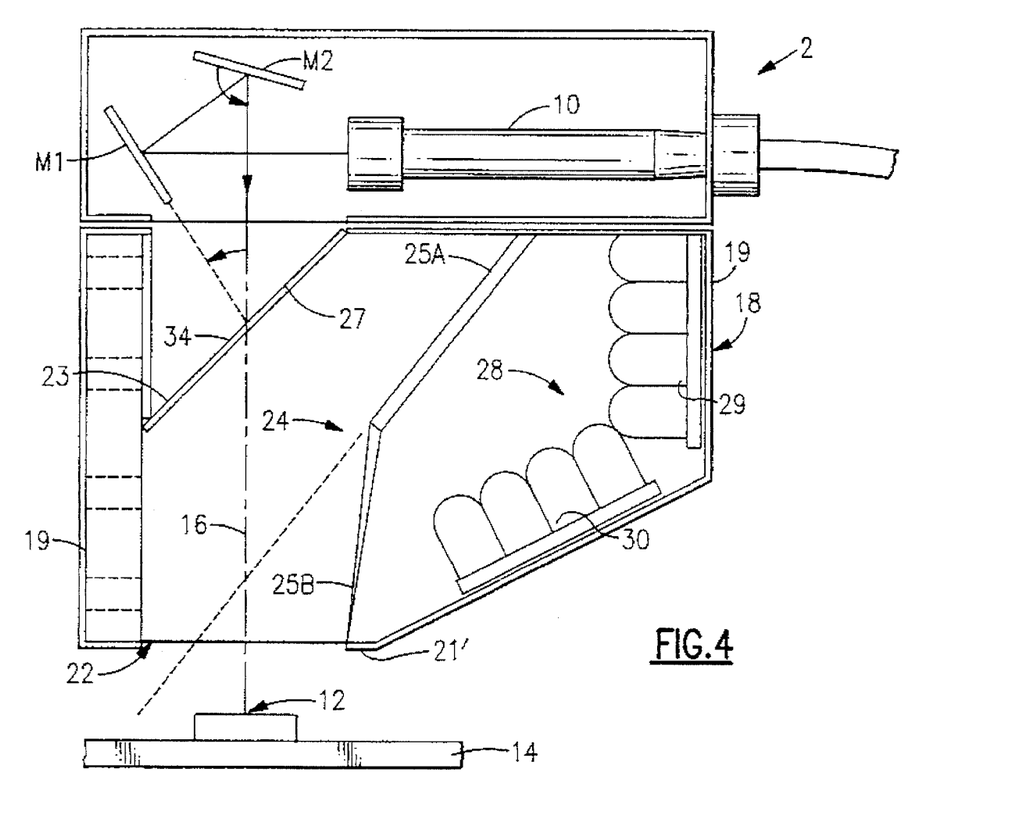
FIG. 4 is a diagrammatic illustration, similar to that of FIG. 1, showing a second embodiment of the attachment of the inspection camera.
Figure 6:
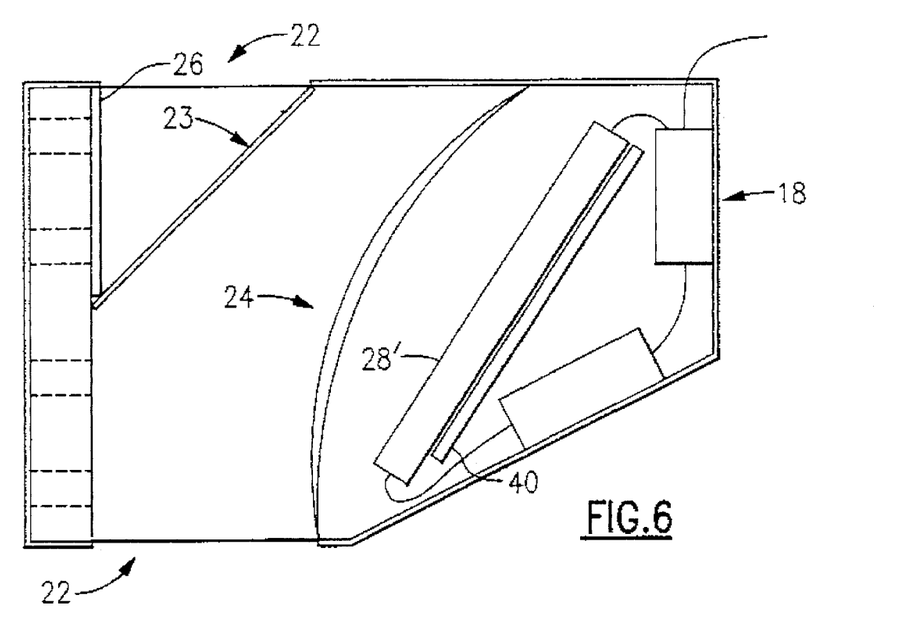
FIG. 6 is a diagrammatic illustration of a third embodiment of an improved continuous diffuse illumination device, providing light both along the observation axis and off-axis, according to the present invention.

Second diffuser portion 25B is made of a translucent diffusing material selected in its material and thickness profile to pass approximately as much light directly to the object 12 as is reflected to the object 12 from the beam splitter 23 (see FIGS. 1, 4 and 6).

Figure 5:
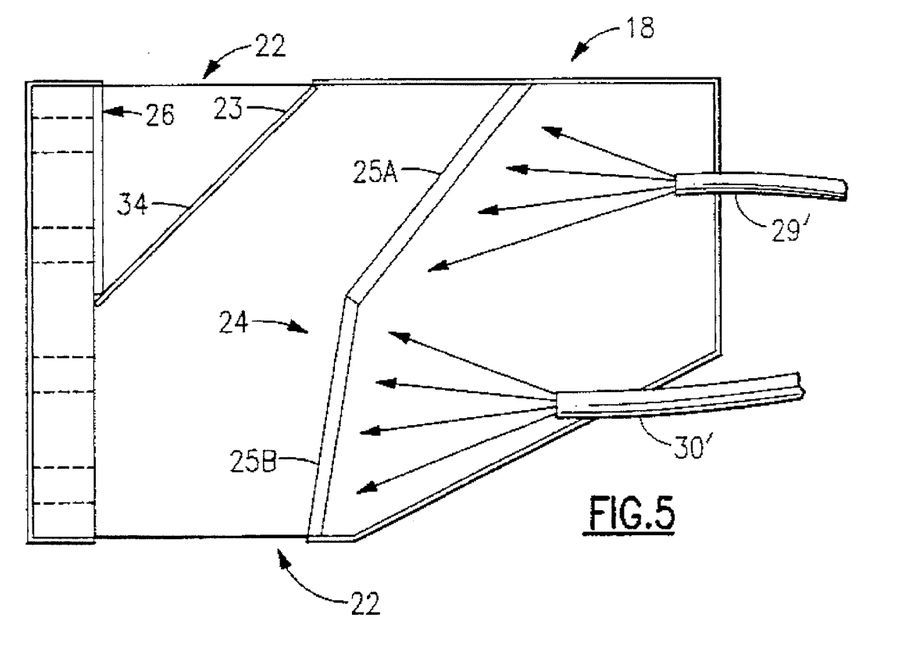
FIG. 5 is a diagrammatic illustration of a second embodiment of an improved continuous diffuse illumination device, providing light both along the observation axis and off-axis, according to the present invention.

The light source 28 is either a single source of light (FIG. 6) in the form of first 29 and second 30 light arrays (FIGS. 1 and 4) or is first and second light members 29', 30' (FIG. 5). The diffuser 24 can likewise either be a single diffuser member, e.g. a curved member having a radius of curvature approximately four times the aperture width 22 for example, in which the curvature is designed to approximate the first and second diffuser portions of the diffuser. Alternatively, the diffuser 24 is in the form of first and second diffuser portions 25A, 25B, e.g. first and second planar diffuser members. The entire inner surface of the housing 18, including the inner surface to the right of the diffuser 24 in FIGS. 1 and 4, is preferably coated with a substance, e.g. paint, which promotes directed reflection of the light generated by the first and second light arrays 29, 30 and reflection of the light diffused by the diffuser.

The present invention is also directed at increasing the apparent brightness of the beam splitter so that the portion of the light which is reflected, toward the object 12 to be observed, by the beam splitter 23 closely matches the brightness of the light reflected by the inner surfaces of the housing 18 whereby a more uniform field of illumination is supplied to the object 12 and an improved viewing of the object 12 by the camera 10 is achieved. There are a number of ways in which the brightness equalization can be accomplished. If a single light source is used to illuminate both the first and second diffuser portions, then the first diffuser portion 25A can be machined to allow twice as much light to pass therethrough than the second diffuser portion 25B. Alternatively, if two light sources are utilized, the intensity of the light source associated with the first diffuser portion 25A can be accordingly increased or two or more light sources may be associated with the first diffuser portion 25A and such two or more light sources light sources may be positioned at different angles.

FIG. 4 shows a second arrangement for mounting the camera to the illumination device 2. In this embodiment, the camera 10 is a micro T.V. camera with a lens and the longitudinal axis of the camera 10 extends substantially perpendicular to the observation axis 16. The camera 10 is provided with a pair of mirrors M1 and M2 for reflecting the light returned along the observation axis 16. For example, here mirrors M1 and M2 are oriented at angles selected to cause the camera's optical axis and the observation axis to substantially coincide. In this FIG., the mirror M1 is oriented at an angle of 64.5° with respect to the observation axis 16 while the mirror M2 is oriented at angle of 112.5° with respect to the observation axis 16 thereby resulting in a perpendicular reflection.

The embodiment of FIG. 5 is similar to the previous embodiment except that the light arrays 29 and 30 are replaced with a pair of fiber optic light guides 29' and 30'. Each one of the fiber optic guides 29' and 30' is directed to shine light on a desired one of the first and second diffuser portions. It is to be appreciated that the number and orientation of the light sources, the light arrays, the fiber optic guide, etc., can be varied depending upon the application at hand.

FIG. 6 is further embodiment of the present invention is shown in which both the diffuser and the light source have been modified. In this embodiment, the diffuser 24 is a curved non-planar member. In addition, the two light arrays 29 and 30 are replaced with a single light source 28' which is a miniature fluorescent light array, electro luminescent panel or fiber optic diffuser, for example. The miniature fluorescent light array is powered by a pair of conventional power supplies (not numbered) and, as such teaching is well known in the art, a further description concerning such light is not provided herein. A rear surface of the miniature fluorescent light array 28' is provided with a planar reflector member 40 which reflects the fluorescent light, directed toward the reflector member 40, back toward the diffuser 24. The diffuser 24 is preferably tapered at least one end, preferably at both ends, depending on the application, to equalize the amount of the light that will pass through the diffuser 24. Typically, when a fluorescent light is used, the generated light is brighter in the central region of the fluorescent light and dimmer at the end regions. The taper of the diffuser at both ends allows the light to pass more readily through the diffuser and thereby compensate for the lower amount of light available in the end regions.

Figure 7:
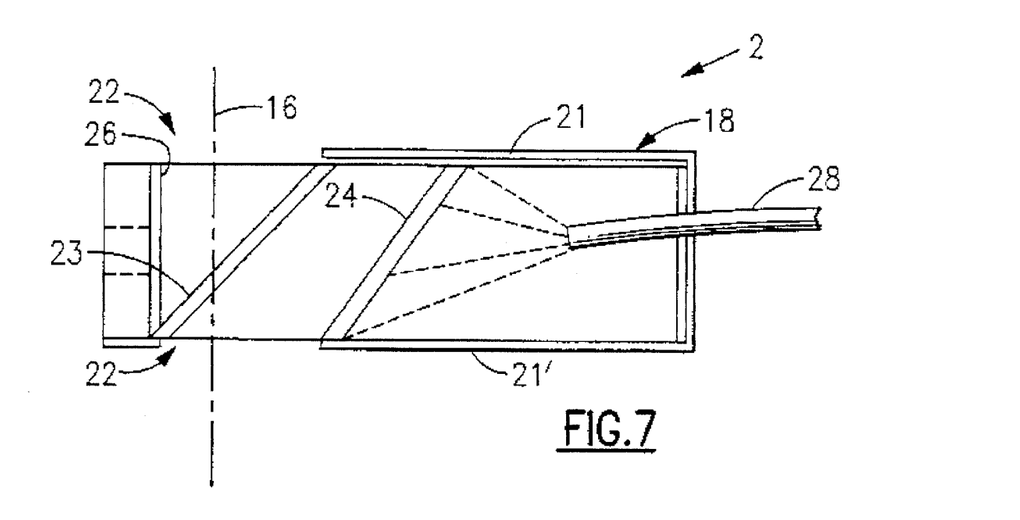
FIG. 7 is a diagrammatic illustration of a fourth embodiment of the present invention.

Turning now to FIG. 7, the broadest form of the present invention will now be discussed in detail. In this embodiment, only a single planar diffuser member is utilized and accommodated within the housing 18. The diffuser is tilted at an angle of approximately 25°–40° with respect to the observation axis 16 so as not to be visible by the object 12 when positioned for observation. In addition, only a single light source 28 is employed. However, due to the tilting of the diffuser 24, the diffuser cannot directly illuminate the object 12 to be observed unless the object is placed substantially in the aperture 22 provided in the base wall 21' of the housing 18. Accordingly, the object 12 is not directly illuminated but receives a desired amount of incident light reflected by the inner surfaces of the side walls and inner roof wall of the housing and thereby results in a more uniform lighting of the object 12 than prior art illumination devices.

Figure 8:
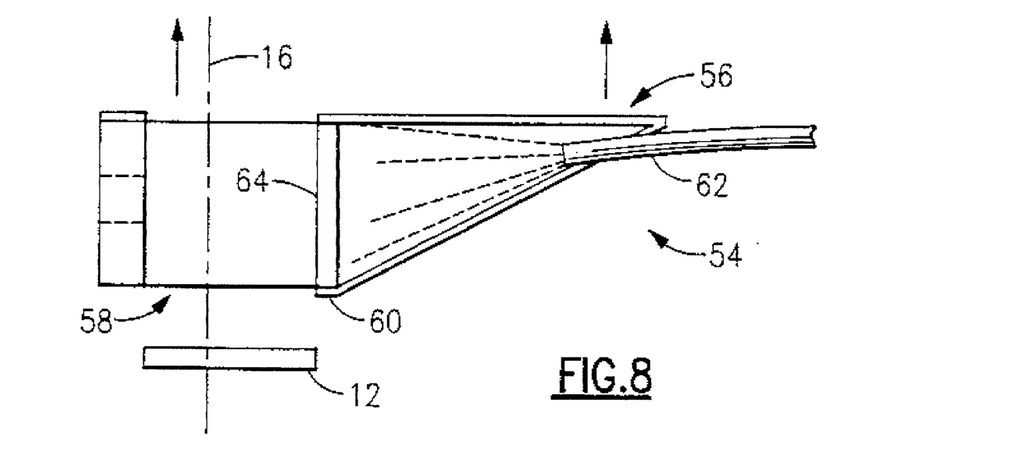
FIG. 8 is a diagrammatic illustration showing an adaptor for the fourth embodiment of FIG. 7 to provide all the advantages of the present invention.

An adaptor to be utilized in combination with the illumination device 2 of FIG. 7 will now be described with reference to FIG. 8. The adaptor 54 comprises a housing 56 having an aperture 58 in the end wall 60 thereof. A roof wall is not necessary and thus the top of the adaptor may be open. The housing 56 contains a light source 62 and a second diffuser 64. The diffuser may extend substantially parallel to the observation axis 16 or may be inclined a small angle relative to that axis, e.g. a few degrees. The adaptor 54 is connected to the base wall 21' of the illumination device 2, as shown by the arrows in FIG. 8. The two components 2 and 54 are securable to one another by any known securing mechanism, e.g. glue, clamps, fasteners, etc., such that the apertures 22, 58 of the two components 2, 54 are aligned along the observation axis 16. The two secured components 2, 54 together function substantially identical to the previous embodiments described above. The preferred division between the first and the second components is shown in FIGS. 7 and 8 and these two components may be sold together or independently of one another.

The beam splitter 23 is preferably in the form of a mirror beam splitter that is well known in the art, but it also could comprise a cube or a membrane. The second surface 34 of the beam splitter 23 (FIG. 1), facing the camera 10, has an anti-reflection coating disposed thereon to prevent stray light from being reflected toward the camera 10 and thereby create a false image. Preferably, magnesium chloride (MgCl) is used as the anti-reflection coating for the beam splitter 23. It is to be appreciated that any other suitable anti-reflection coating, that permits the camera 10 to observe the object 12 through the beam splitter 23 free of a double image or a ghost image, may be utilized on the second surface 34 of the beam splitter 23.

The diffuser 24 may consist of a pair of planar plate members formed of glass or plastic, as shown in FIGS. 1 and 4, each lying in a different plane and having a surface which is translucent and capable of diffusing light passing through the diffuser. The diffuser 24 may alternatively be formed of an etched or ground glass, or may be formed of opal glass having light scattering centers of colloidal particles. Frosted glass, milky plastic or a Murata screen may also be used. Murata screen is formed of a diffusing synthetic plastic material.

It is important that the diffuser 24 have wide-angle diffuser characteristics so that light cast thereon is evenly diffused by the diffuser so that a substantially uniform intensity of light passes through the diffuser for reflection toward the object 12 by the beam splitter 23.

A variety of different light sources may be used as the light arrays 28 and 29. For example, the light arrays 28 and 29 may be a rectangular configuration having a plurality of bulbs evenly spaced thereon. Alternatively, the light arrays may be incandescent fiber optics, LEDs or fluorescent lights 5. The important requirement of the light source is that it be capable of supplying a substantially uniform intensity of light to the diffuser 24 so that the diffuser 24 may evenly diffuse the light received from the light source 28 and uniformly illuminate the object 12 both on-axis and off-axis.

Preferably, the beam splitter 23 is disposed at an angle of 45° with respect to the observation axis 16, however, it will be appreciated that the angle of the beam splitter may be varied, as desired, from a 45° orientation and still function in the desired manner. If the beam splitter 23 is located at a 45° orientation with respect to the observation axis 16, it is necessary to approximately double the length of the side walls 19 and 20 to achieve substantially uniform illumination of the object 12. If the orientation is varied from 45° orientation, the length of the side walls 19 and 20 would be accordingly varied in order to provide uniform lighting of the desired object 12. The length of the side walls is determined such that the continuity of incident light, which falls on the object, is substantially uniform. In addition, the size, shape and orientation of the object 12 to be observed must be taken into account, along with the tilt angle of the first diffuser portion with respect to the observation axis, when determining the length to the side walls.

For maximum uniformity of illumination, the beam splitter 23' should be curved sufficiently (FIGS. 10 and 11) to eliminate the beam splitter 23' from reflecting light, diffused by the first diffuser portion 25A and reflected off the side walls located between the beam splitter 23' and the first diffuser portion 25A, toward the object 12 being observed, i.e. the beam splitter 23' only reflects light directed toward the beam splitter and does not reflect any light reflecting off the adjacent side walls. In the case of an illumination device 2 having a 2 inch square aperture and a beam splitter inclined at an angle of 45° with respect to the object, the calculated radius of curvature required is 11.482 inches, which is just sufficient to cause diverging rays to be collimated from the beam splitter 23' back to the diffuser for a 2 inch square aperture. The required curvature is a function of camera 10 and part distance, however the true scale dimensions shown in FIG. 11 represent a good approximation of a typical case. As a rule of thumb, then, the radius of curvature should be slightly less than 11.242/2=5.621 or, to be safe, a radius of 5.5 times the aperture dimension. This can achieved with a flexible beam splitter by making the width of the beam splitter be between 101% and 102% of its nominal flat width, and then fitting the oversize beam splitter within its original nominal width holding fixture, thereby flexing the beam splitter to the desired partially cylindrical curvature.

Figure 13:
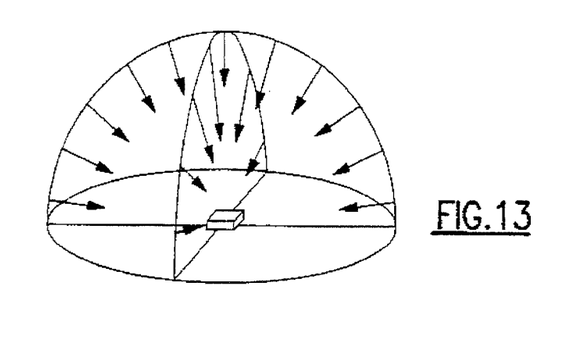
FIG. 13 is a graph of desired hemispheric lighting envelope.

FIG. 12 is a graph depicting the characteristics of a diffuse light source while FIG. 13 depicts a lighting envelope which has uniformity in a complete range of incidents of the lightening envelope which is particularly adapted to determine the appearance of specular (shiny) objects and surfaces. Variations of the appearance of the specular objects and surfaces are minimized by having a continuous unbroken field of illumination and a maximum uniformity of the incident light.

The light trap 26 may consist of a planar panel defining a straight wall parallel to the observation axis 16. The light trap 26 is preferably of a flat black color so as to be capable of maximum light absorption. Alternative, a portion of the inner surface of the side wall 19 may be painted black, for example, to function as the light trap. By locating the light trap in alignment with the diffuser 24 and the beam splitter 24, light from the diffuser 24 passing through the beam splitter 23 will be absorbed by the light trap 26 and not be reflected into the camera 10 where it could produce an erroneous signal.

A portion of the light diffused by the diffuser 24 will be reflected by the beam splitter surface 27 in a uniform manner upon the object 12. This uniform illumination of the object 12, in a symmetrical on-axis relationship to the observation axis 16, permits the camera 10 to produce a highly accurate and unambiguous image of the object 12 free of spurious glints and shadows thereby to precisely view and determine the exact location, orientation and other visual qualities of the object being observed, particularly for shiny and uneven surfaces. This facilitates accurate robotic control of the positioning and manipulation of the object 12.

An important advantage achieved by the illumination device according to the present invention, is that a substantially uniform and diffuse lighting of the object 12 to be observed is achieved. This is accomplished, in part, by adjusting the brightness of the on-axis light, diffused by the diffuser 24 and reflected by the beam splitter 23, to be substantially equal in brightness to the off-axis light which is reflected by the inner surfaces of the housing side walls.

Since certain changes may be made in the above described illumination device without departing from the spirit and scope of the invention herein involved, it is intended that all matter contained in the above description or shown in the accompanying drawings shall be interpreted merely as examples illustrating the inventive concept herein and shall not be construed as limiting the invention.

I claim:

1. An illumination device for illuminating an object to be observed by a camera along an observation axis extending from the camera to the object, said illumination device comprising:

a housing having at least one aperture therein aligned with an observation axis;

a partially reflective beam splitter being supported by said housing and being positioned obliquely relative to the observation axis adjacent said at least one aperture;

a light source being arranged to cast light on a first surface of said beam splitter; and a diffuser being positioned between said first surface of said beam splitter and said light source for diffusing light from said light source as the light passes through said diffuser to said beam splitter;

wherein at least a first portion of said diffuser, facing said beam splitter, is inclined a sufficient distance relative to the observation axis so that at least the first portion of the surface of said diffuser facing said beam splitter is invisible by any portion of an object to be observed when the object is positioned along the observation axis.

2. The illumination device according to claim 1, wherein said housing has a second aperture therein also aligned with the observation axis and said beam splitter is located between said first aperture and said second aperture.

3. The illumination device according to claim 2, wherein said diffuser comprises first and second diffuser portions, said first diffuser portion is completely hidden from direct viewing by the object to be observed, when the object is positioned on the observation axis, while said second diffuser portion is positioned to be directly visible by the object to be observed, when the object is positioned on the observation axis, and thereby facilitate direct off-axis lighting of the object to be observed.

4. The illumination device according to claim 2, wherein said first and second diffuser portions are both planar and planes defined by said first and second diffuser portions form an angle of between about 5° and about 45° with respect to one another.

5. The illumination device according to claim 3, wherein at least an end portion of said second diffuser portion is tapered in thickness to facilitate passage of light through the tapered end portion of said second diffuser portion.

6. The illumination device according to claim 2, wherein said diffuser is a curved member which has a radius of curvature of between about 3 to about 6 times the aperture of the unit.

7. The illumination device according to claim 3, wherein said light source comprises at least two different sources, one of said at least two different sources illuminates said first diffuser portion and the other one of said at least two different sources also illuminates said first diffuser portion and said at least two different sources are arranged to only indirectly illuminate said second diffuser portion.

8. The illumination device according to claim 3, wherein said light source comprises at least two different sources, one of said at least two different sources illuminates said first diffuser portion and the other one of said at least two different sources also illuminates said second diffuser portion.

9. The illumination device according to claim 7, wherein said light source comprises one of bulbs, incandescent fiber optics, LEDs and fluorescent light.

10. The illumination device according to claim 2, wherein said light source comprises at least one array of lights.

11. The illumination device according to claim 2, wherein said illumination device includes a light trap located adjacent said beam splitter but positioned remote from said diffuser such that said light trap is positioned to absorb unreflected diffuse light which passes through said beam splitter.

12. The illumination device according to claim 2, wherein the inner surface of the housing is coated with a substance reflects a desired amount of light so as to match a brightness of the light reflected by said beam splitter.

13. The illumination device according to claim 1, wherein said illumination device is used in combination with an inspection camera, and said inspection camera is position adjacent the second aperture of said housing to sense light reflected by the object to be observed.

14. The illumination device according to claim 2, wherein said illumination device is used in combination with an inspection camera, and said inspection camera is position adjacent the second aperture of said housing to sense light reflected by the object to be observed.

15. The combination according to claim 14 wherein the combination further includes a computer and assembly equipment and the computer is connected with the camera and the assembly equipment to control and manipulate the object to be observed as desired.

16. In an illumination device, for illuminating an object to be observed by a camera along an observation axis extending from the camera to the object, comprising a housing having at least one aperture therein aligned with an observation axis; a partially reflective beam splitter being supported by said housing and being positioned obliquely relative to the observation axis adjacent said at least one aperture; a light source being arranged to cast light on a first surface of said beam splitter; and a diffuser being positioned between said first surface of said beam splitter and said light source for diffusing light from said light source as the light passes through said diffuser to said beam splitter;

wherein at least a first portion of said diffuser facing said beam splitter is inclined a sufficient distance relative to the observation axis such that an emitting surface of said diffuser is completely hidden from direct viewing by the object to be observed, when the object is positioned on the observation axis and during use of said illumination device, whereby at least the first portion of said diffuser only indirectly illuminates the object to be observed by reflect.

17. A method of illuminating an object to be observed by a camera along an observation axis extending from the camera to the object, said method comprising the steps of:

utilizing a housing having at least one aperture therein aligned with an observation axis;

supporting a partially reflective beam splitter within said housing, and positioning said partially reflective beam splitter obliquely relative to the observation axis adjacent said at least one aperture;

arranging a light source to cast light on a first surface of said beam splitter; and positioning a diffuser between said first surface of said beam splitter and said light source for diffusing light from said light source as the light passes through said diffuser to said beam splitter; and inclining at least a first portion of said diffuser facing said beam splitter a sufficient distance relative to the observation axis so that at least the first portion of the surface of said diffuser facing said beam splitter is not directly visible by any portion of an object to be observed when the object is positioned along the observation axis.

18. The method according to claim 17, further comprising the steps of adjusting a brightness of the diffused light reflected by said beam splitter to be substantially equal in intensity and character to the light reflected by an inner surface of said housing and any direct light received, from said diffuser, by the object to be observed.

19. The method according to claim 17, further comprising the step of utilizing first and second diffuser portions, and directly illuminating said first diffuser portion and only indirectly illuminating said second diffuser portion.

20. The illumination device according to claim 3, wherein said beam splitter is curved to collimate a reflected image of the first diffuser portion toward the object being observed.

* * * * *